(12) United States Patent
Diaz et al.

(10) Patent No.: US 7,195,644 B2
(45) Date of Patent: Mar. 27, 2007

(54) BALL AND DUAL SOCKET JOINT

(75) Inventors: Robert Diaz, Palm Beach Gardens, FL (US); Robert Doubler, Ida, MI (US); John E. Hamill, Rossford, OH (US)

(73) Assignee: Joint Synergy, LLC, Palm Beach Gardens, FL (US)

( * ) Notice: Subject to any disclaimer, the term of this patent is extended or adjusted under 35 U.S.C. 154(b) by 214 days.

(21) Appl. No.: 11/060,206

(22) Filed: Feb. 15, 2005

(65) Prior Publication Data

US 2006/0142862 A1 Jun. 29, 2006

Related U.S. Application Data

(63) Continuation-in-part of application No. 11/025,656, filed on Dec. 28, 2004, now abandoned.

(51) Int. Cl.
*A61F 2/44* (2006.01)

(52) U.S. Cl. .............................. 623/17.13; 623/17.15; 623/17.14

(58) Field of Classification Search .. 623/17.11–17.16; 606/53–61; 128/898, 899
See application file for complete search history.

(56) References Cited

U.S. PATENT DOCUMENTS

| 566,360 | A | 8/1896 | White |
|---|---|---|---|
| 1,436,573 | A | 11/1922 | Choppinet et al. |
| 2,836,442 | A | 5/1958 | Moskovitz |
| 3,325,197 | A | 6/1967 | Wehner |
| 3,426,364 | A | 2/1969 | Lumb |
| 3,857,642 | A | 12/1974 | Miller |
| 3,875,595 | A | 4/1975 | Froning |
| 4,074,542 | A | 2/1978 | Hankosky et al. |
| 4,156,070 | A | 5/1979 | Jackson, Jr. et al. |
| 4,238,600 | A | 12/1980 | Jackson, Jr. et al. |
| 4,257,129 | A | 3/1981 | Volz |
| 4,289,123 | A | 9/1981 | Dunn |
| 4,309,777 | A | 1/1982 | Patil |
| 4,349,921 | A | 9/1982 | Kuntz |
| 4,401,112 | A | 8/1983 | Rezaian |
| 4,412,058 | A | 10/1983 | Siemionko |
| 4,499,259 | A | 2/1985 | Irwin |
| 4,605,417 | A | 8/1986 | Fleischauer |
| 4,614,789 | A | 9/1986 | Dicke et al. |
| 4,636,217 | A | 1/1987 | Ogilvie et al. |
| 4,655,778 | A | 4/1987 | Koeneman |
| 4,664,972 | A | 5/1987 | Connolly |

(Continued)

*Primary Examiner*—Alvin J. Stewart
*Assistant Examiner*—Ann Schillinger
(74) *Attorney, Agent, or Firm*—McHale & Slavin PA

(57) ABSTRACT

A spinal implant is inserted between adjacent vertebrae to function as an disk prosthesis. The prosthesis has two plates fastened to adjacent vertebrae facing each other. The facing sides of the plates each have a depending skirt formed as concentric arcs of about 90 degrees. The skirts are either bowed or tapered in the axial direction. Depressions are centrally located between the arcs of the plates and a ball is universally movable in the depressions. A spring mechanism is centrally located in the plates to provide axial compression. The plates are oriented to each other with the concentric arcs of each interrupted skirt at 90 degrees and the protrusion is engaged in the depression. The plates are then rotated about 90 degrees and the opposed arcs of one plate interlock with the opposed arcs of the other plate to prevent separation in the axial direction.

19 Claims, 5 Drawing Sheets

U.S. PATENT DOCUMENTS

| | | | | |
|---|---|---|---|---|
| RE32,449 E | | 6/1987 | Claussen et al. | |
| 4,714,469 A | | 12/1987 | Kenna | |
| 4,749,769 A | | 6/1988 | Kock et al. | |
| 4,756,711 A | | 7/1988 | Mai et al. | |
| 4,759,766 A | * | 7/1988 | Buettner-Janz et al. | 623/17.15 |
| 4,759,769 A | | 7/1988 | Hedman et al. | |
| 4,770,659 A | | 9/1988 | Kendall | |
| 4,787,908 A | | 11/1988 | Wyss et al. | |
| 4,863,476 A | | 9/1989 | Shepperd | |
| 4,863,477 A | | 9/1989 | Monson | |
| 4,874,389 A | | 10/1989 | Downey | |
| 4,892,545 A | | 1/1990 | Day et al. | |
| 4,904,261 A | | 2/1990 | Dove et al. | |
| 4,919,666 A | | 4/1990 | Buchhorn et al. | |
| 4,932,969 A | | 6/1990 | Frey et al. | |
| 4,932,975 A | * | 6/1990 | Main et al. | 623/17.12 |
| 4,936,848 A | | 6/1990 | Bagby | |
| 4,946,378 A | | 8/1990 | Hirayama et al. | |
| 4,946,458 A | | 8/1990 | Harms et al. | |
| 4,955,908 A | | 9/1990 | Frey et al. | |
| 4,955,916 A | | 9/1990 | Carignan et al. | |
| 4,997,432 A | | 3/1991 | Keller | |
| 5,002,576 A | | 3/1991 | Fuhrmann et al. | |
| 5,024,670 A | | 6/1991 | Smith et al. | |
| 5,041,139 A | | 8/1991 | Branemark | |
| 5,047,055 A | | 9/1991 | Bao et al. | |
| 5,071,437 A | | 12/1991 | Steffee | |
| 5,123,926 A | | 6/1992 | Pisharodi | |
| 5,145,134 A | | 9/1992 | Hashimoto et al. | |
| 5,192,326 A | | 3/1993 | Bao et al. | |
| 5,236,460 A | | 8/1993 | Barber | |
| 5,246,458 A | * | 9/1993 | Graham | 623/17.14 |
| 5,258,031 A | | 11/1993 | Salib et al. | |
| 5,258,043 A | | 11/1993 | Stone | |
| 5,306,307 A | | 4/1994 | Senter et al. | |
| 5,306,308 A | | 4/1994 | Gross et al. | |
| 5,306,309 A | | 4/1994 | Wagner et al. | |
| 5,308,412 A | | 5/1994 | Shetty et al. | |
| 5,314,477 A | | 5/1994 | Marnay | |
| 5,320,644 A | | 6/1994 | Baumgartner | |
| 5,360,430 A | | 11/1994 | Lin | |
| 5,370,697 A | | 12/1994 | Baumgartner | |
| 5,401,269 A | * | 3/1995 | Buttner-Janz et al. | 623/17.15 |
| 5,404,182 A | | 4/1995 | Nomura | |
| 5,414,704 A | | 5/1995 | Spinney | |
| 5,425,773 A | * | 6/1995 | Boyd et al. | 623/17.15 |
| 5,425,777 A | | 6/1995 | Sarkisian et al. | |
| 5,458,638 A | | 10/1995 | Kuslich et al. | |
| 5,458,641 A | | 10/1995 | Ramirez Jimenez | |
| 5,458,642 A | | 10/1995 | Beer et al. | |
| 5,474,555 A | | 12/1995 | Puno et al. | |
| 5,489,308 A | | 2/1996 | Kuslich et al. | |
| 5,507,816 A | | 4/1996 | Bullivant | |
| 5,534,029 A | | 7/1996 | Shima | |
| 5,534,030 A | | 7/1996 | Navarro et al. | |
| 5,538,427 A | | 7/1996 | Hoffman et al. | |
| 5,549,680 A | | 8/1996 | Gordon | |
| 5,556,431 A | | 9/1996 | Buttner-Janz | |
| 5,562,738 A | * | 10/1996 | Boyd et al. | 623/17.15 |
| 5,566,687 A | | 10/1996 | Trapanovski | |
| 5,588,625 A | | 12/1996 | Beak | |
| 5,603,478 A | | 2/1997 | Wang | |
| 5,645,596 A | | 7/1997 | Kim et al. | |
| 5,674,296 A | | 10/1997 | Bryan et al. | |
| 5,676,701 A | * | 10/1997 | Yuan et al. | 623/17.15 |
| 5,683,465 A | * | 11/1997 | Shinn et al. | 623/17.14 |
| 5,782,832 A | | 7/1998 | Larsen et al. | |
| 5,893,889 A | * | 4/1999 | Harrington | 623/17.16 |
| 5,895,428 A | * | 4/1999 | Berry | 623/17.15 |
| 5,899,941 A | | 5/1999 | Nishijima et al. | |
| 5,989,291 A | * | 11/1999 | Ralph et al. | 623/17.15 |
| 6,001,130 A | * | 12/1999 | Bryan et al. | 623/17.16 |
| 6,019,792 A | * | 2/2000 | Cauthen | 623/17.14 |
| 6,039,763 A | | 3/2000 | Shelokov | |
| 6,063,121 A | | 5/2000 | Xavier et al. | |
| 6,146,421 A | | 11/2000 | Gordon et al. | |
| 6,179,874 B1 | * | 1/2001 | Cauthen | 623/17.14 |
| 6,228,118 B1 | | 5/2001 | Gordon | |
| 6,416,551 B1 | | 7/2002 | Keller | |
| 6,517,580 B1 | | 2/2003 | Ramadan et al. | |
| 6,579,321 B1 | * | 6/2003 | Gordon et al. | 623/17.16 |
| 6,682,562 B2 | * | 1/2004 | Viart et al. | 623/17.14 |
| 6,709,458 B2 | * | 3/2004 | Michelson | 623/17.15 |
| 6,723,127 B2 | * | 4/2004 | Ralph et al. | 623/17.13 |
| 6,749,635 B1 | * | 6/2004 | Bryan | 623/17.16 |
| 6,770,094 B2 | * | 8/2004 | Fehling et al. | 623/17.13 |
| 6,800,092 B1 | * | 10/2004 | Williams et al. | 623/17.11 |
| 6,846,328 B2 | * | 1/2005 | Cauthen | 623/17.11 |
| 6,893,465 B2 | * | 5/2005 | Huang | 623/17.12 |
| 6,936,071 B1 | * | 8/2005 | Marnay et al. | 623/17.15 |
| 6,969,405 B2 | * | 11/2005 | Suddaby | 623/17.12 |
| 6,981,989 B1 | * | 1/2006 | Fleischmann et al. | 623/17.11 |
| 6,986,789 B2 | * | 1/2006 | Schultz et al. | 623/17.15 |
| 6,989,032 B2 | * | 1/2006 | Errico et al. | 623/17.14 |
| 7,014,658 B2 | * | 3/2006 | Ralph et al. | 623/17.13 |
| 7,044,969 B2 | * | 5/2006 | Errico et al. | 623/17.14 |
| 7,060,098 B2 | * | 6/2006 | Errico et al. | 623/17.14 |
| 7,083,651 B2 | * | 8/2006 | Diaz et al. | 623/17.13 |
| 7,115,144 B2 | * | 10/2006 | Diaz et al. | 623/17.14 |
| 2002/0111686 A1 | * | 8/2002 | Ralph et al. | 623/17.13 |
| 2003/0204261 A1 | * | 10/2003 | Eisermann et al. | 623/17.14 |
| 2004/0138750 A1 | * | 7/2004 | Mitchell | 623/17.11 |
| 2004/0236425 A1 | * | 11/2004 | Huang | 623/17.12 |
| 2004/0243238 A1 | * | 12/2004 | Arnin et al. | 623/17.12 |
| 2005/0043804 A1 | * | 2/2005 | Gordon et al. | 623/17.16 |
| 2005/0234553 A1 | * | 10/2005 | Gordon | 623/17.13 |
| 2005/0246022 A1 | * | 11/2005 | Zubok et al. | 623/17.11 |
| 2005/0251260 A1 | * | 11/2005 | Gerber et al. | 623/17.13 |
| 2006/0142862 A1 | * | 6/2006 | Diaz et al. | 623/17.13 |
| 2006/0190084 A1 | * | 8/2006 | Doubler et al. | 623/17.14 |
| 2006/0235525 A1 | * | 10/2006 | Gil et al. | 623/17.13 |

* cited by examiner

BALL AND DUAL SOCKET JOINT

RELATED APPLICATIONS

This application is a continuation-in-part of a U.S. patent application Ser. No. 11/025,656, entitled Ball-In-Cage Spinal Implant, filed Dec. 28, 2004 now abandoned which is related to U.S. application Ser. No. 10/793,433, filed Mar. 3, 2004 which is a continuation-in-part of U.S. application Ser. No. 10/792,399, filed Mar. 2, 2004.

FIELD OF THE INVENTION

This invention relates to orthopedic surgery and, in particular, spinal implants for replacement of ruptured or excised spinal disks.

BACKGROUND OF THE INVENTION

Several attempts have been made to design a spinal prosthesis for replacement of missing or excised disk material that replicates the functions of the missing tissue. U.S. Pat. No. 4,759,769 to Hedman et al discloses an artificial disk device in which two plates are attached to the adjacent vertebrae by bone screws inserted through flanges on the plates. A spring biasing mechanism is captured between the plates to simulate the actions of the natural disk material. U.S. Pat. No. 5,246,458 to Graham and U.S. Pat. No. 6,228,118 to Gordon disclose other intervertebral implants with arcuate flanges used to connect the device to adjacent vertebra. Graham also teaches a resilient structure.

The patents to Marnay, U.S. Pat. No. 5,314,477, Buttner-Janz et al, U.S. Pat. No. 5,401,269, Yuan et al, U.S. Pat. No. 5,676,701, and Shelokov, U.S. Pat. No. 6,039,763, all are directed to the design of the opposing faces of the adjacent plates of an implant to provide a limited universal joint to simulate the natural movement of the spine.

U.S. Pat. No. 5,683,465 to Shinn et al teaches two plates with bow shaped skirts which are interlocked.

SUMMARY OF THE PRESENT INVENTION

The invention is directed to a spinal implant for insertion between adjacent vertebrae to function as an disk prosthesis. The prosthesis is formed from two plates fastened to adjacent vertebrae facing each other. The facing sides of the plates each have a depending skirt formed as concentric arcs of about 90 degrees. The skirts are either bowed or tapered in the axial direction. A depression is centrally located between the arcs of both plates. A spring mechanism is centrally located on one or both of the plates to provide axial compression. A sphere or ball is placed in the central depression of one of the plates. The plates are oriented to each other with the concentric arcs of each interrupted skirt at 90 degrees and the ball is engaged in the depression of the other plate. The plates are then rotated about 90 degrees and the opposed arcs of one plate interlock with the opposed arcs of the other plate to prevent separation in the axial direction.

Therefore, it is an objective of this invention to provide a spinal implant for axial support of the spinal column which replicates the dimensions and function of an intervertebral disk.

It is another objective of this invention to provide a kit including all the components for assembly and surgical placement of an artificial spinal disk.

It is a further objective of this invention to provide a method of assembly of the components of the kit which results in an axially interlocked spinal implant.

It is yet another objective of this invention to provide a ball and socket joint between two plates attached to adjacent vertebrae permitting axial rotation, lateral bending, vertical tilting and axial compression.

It is a still further objective of this invention to provide shaped interrupted skirts on two plates which act as stop limits for tilting and bending.

It is another objective of this invention to provide an axially resilient ball and socket joint.

It is a further objective of this invention to provide a polymeric material between the two plates for replicating the function of the natural disk and preventing boney ingrowth.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
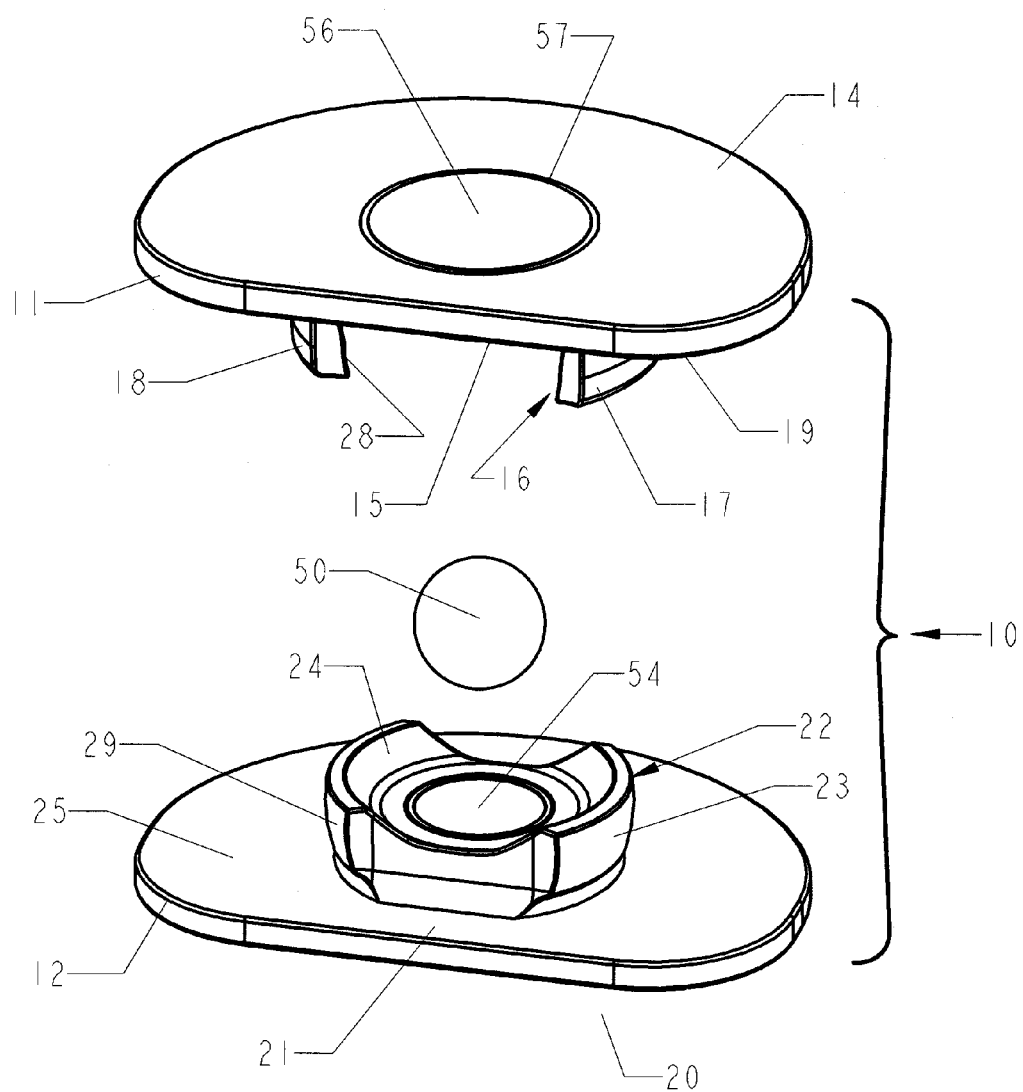
FIG. 1 is an exploded perspective of the disassembled cage of this invention.

The spinal implant 10, shown in FIG. 1, has three major components, an upper plate 11, a lower plate 12 and a universally rotatable sphere or ball 50. The upper plate 11 and the lower plate 12 form a cage when assembled with the ball 50 captured for universal movement within the interior of the cage. Of course, the position of the plates can be reversed, in use. Both upper plate 11 and lower plate 12 have a plan form substantially the size and shape of the end wall of the vertebra between which the implant will be placed to produce the maximum area of contact between the implant and the vertebra for stability and support. Obviously, different sized plates are necessary because of the difference in size of vertebra within regions of the spinal column and the different sizes or ages of patients.

The upper plate 11 has a planar surface 14 for contact with the end wall of a vertebra and an opposite disk surface 15. Depending from the disk surface is an interrupted skirt 16 with opposed arcs 17 and 18. The arcs are approximately 180 degrees apart at their centers and extend about 90 degrees. The diameter of the arcs is less than the periphery of the plate 11 leaving a horizontal flange 19. Centrally located within the semi-circular arcs is a through bore 13. A sleeve 51 is inserted in the through bore 13 and telescopes in the plate 11. The sleeve 51 has a spherical depression 52 facing plate 12.

The lower plate 12 has a planar surface 20 for contact with the end wall of a vertebra and an opposite disk surface 21. Upstanding from the disk surface is an interrupted skirt 22 with opposed arcs 23 and 24. The arcs are approximately 180 degrees apart at their centers and extend about 90 degrees. The diameter of the arcs is less than the periphery of the plate 12 leaving a horizontal flange 25. Centrally located within the semi-circular arcs is a through bore 26. A sleeve 53 is inserted in the through bore and reciprocates in the plate 12. The sleeve 53 has a depression 54 that is rounded and shaped to closely mirror the contours of the depression 52. The depressions 52 and 54, as well as the diameter of the ball 50, are of such dimensions as to support the weight of the spinal column.

As shown, though the relationship could be reversed, the opposed arcs 17 and 18 of the depending interrupted skirt 16 are concentric with the opposed arcs 23 and 24 of the upstanding interrupted skirt and of lesser diameter allowing rotation of the plates relative to each other with surface contact between the outer surface 28 of the depending arcs and the inner surface 29 of the upstanding arcs.

The spinal implant provides support and range of motion similar to the natural joint in that the plates 11 and 12 may rotate axially limited by natural anatomical structures, such as tendons, ligaments and muscles. To simulate the compression of the natural disk during normal activities, such as walking, a spring mechanism 60, 61 is placed in the vertical axis of the plates 11 and 12. The springs are resiliently compressionable.

The spring retainer 63 is in the opposite end of sleeve 51 from the depression 52. The annular spring retainer 63 is formed by the upstanding end wall of the sleeve and the dome shaped central portion. An O-ring spring 60 is disposed in the spring retainer 63. The spring 60 and the sleeve 51 are held in the plate 11 by dome cover plate 56.

The sleeve 53 is resiliently supported on the spring 61 in the form of a resilient O-ring. The spring is held in the cavity 64 by the dome cover plate 55. Each of the dome cover plates has a laser weld 57, 58 or other bond to their respective plates. By absorbing some of the longitudinal loads, the prosthesis lessens the stresses on the adjacent natural disks. Further, during placement of the prosthesis, the springs may be compressed to lessen the overall height of the prosthesis.

Figure 4:
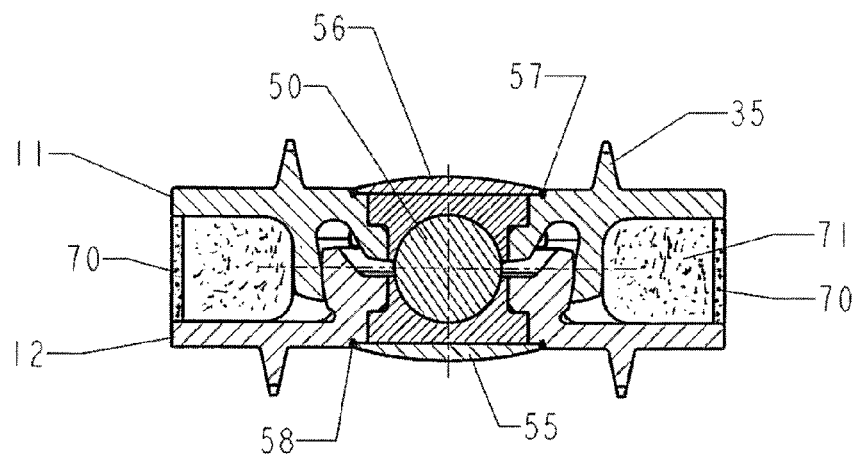
FIG. 4 is a cross section of another embodiment of the assembled implant of this invention.
Figure 5:
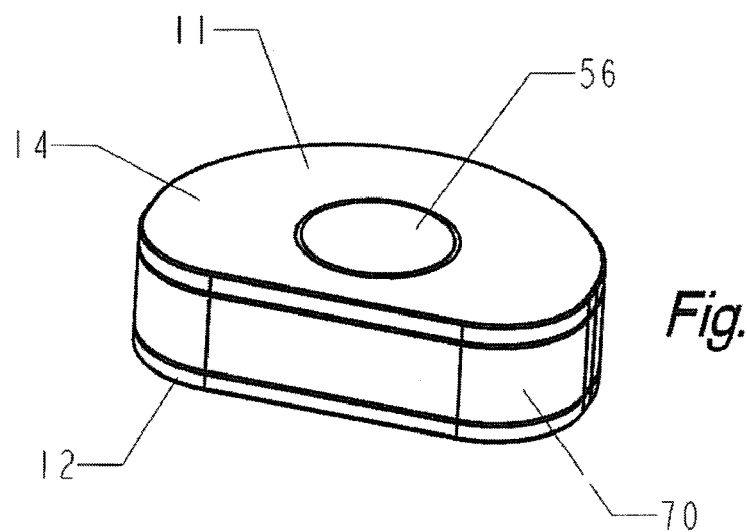
FIG. 5 is a perspective of the embodiment shown in FIG. 4.
Figure 6:
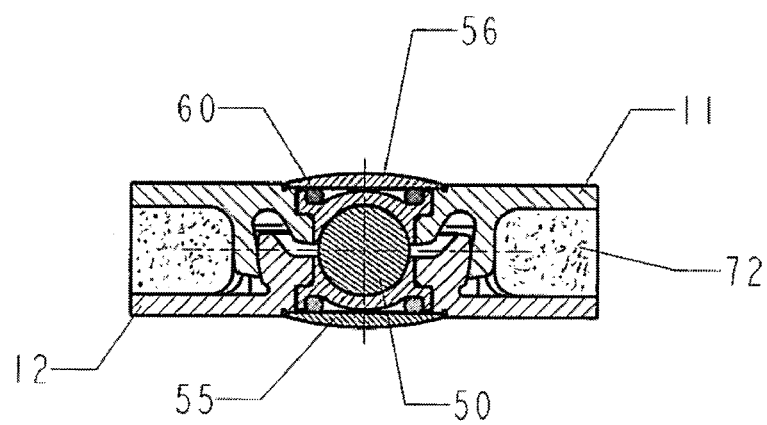
FIG. 6 is a cross section of another embodiment of the assembled implant of this invention.

To further imitate the function of a natural disk, the plates 11 and 12 may have a resilient material inserted therebetween, as shown in FIGS. 4, 5, and 6. The plates may be connected by a flexible or elastomeric membrane 70, as shown in FIG. 4. The membrane 70 can be discontinuous and, act as a plurality of elastic bands about the periphery of the plates 11 and 12. Or the membrane 70 may be a continuous annular wall attached to the opposite flanges 19 and 25. A viscous polymeric compound 71 may occupy the space between the plates, such as a high molecular weight polyethylene or silicone. The membrane may be in the form of an outer skin integral with the polymeric compound. The viscosity of the material may vary from that of a gel to that of a solid. The polymeric compound may be molded or otherwise sealed between the plates 11 and 12. The continuous membrane discourages boney ingrowth which can limit spinal movement. As the neck is turned or tilted, the insert will be compressed on one side and extended on the other side producing a cushioning effect and a tendency to return to a state of equilibrium.

As shown in FIG. 6, an elastomeric plug 72 may be inserted between the plates and attached to one or both the plates 11 and 12. The plug 72 operates in the same manner as the polymeric compound discussed above.

The spine may bend laterally and tilt medially in flexion/extension in a range comparable to the normal range of motion. The inserts 71 and 72 may also having varying viscosities or moments of elasticity tailored to the area of the spine in which they are to be implanted.

Figure 3:
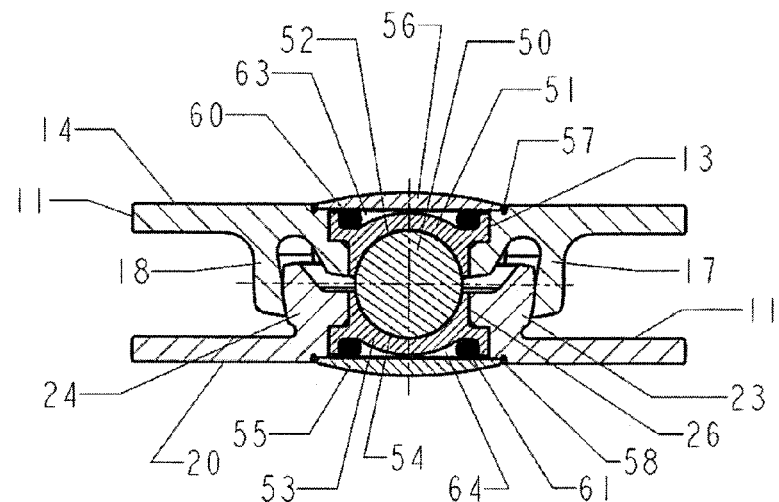
FIG. 3 is a cross section of the assembled implant of this invention.

The implant also provides limitation of these movements through interaction of the depending arcs and the upstanding arcs. As shown in FIG. 3, the components of the implant are connected together by orienting the interrupted skirts 16 and 22 at 90 degrees to each other. This action overlaps the interrupted skirts vertically. The plates are rotated through 90 degrees relative to each other. This rotation aligns the depending opposed arcs with the upstanding opposed arcs and interlocks the plates in a movable joint that cannot be separated axially. The inner surface 28 of the interrupted skirt 16 slidably contacts the outer surface 29 of the interrupted skirt 22. The contacting surfaces are spherical or bowed, from the plate at least to the height of the diameter of the ball 50, forming another ball and socket joint with the bottom edge of the depending arc 23 of a larger diameter than the top edge of the upstanding arc 17 by which the plates are interlocked. Of course, the remainder of the inner and outer surfaces of the interrupted skirts may be straight or tapered and spaced apart to allow for bending and tilting. In this instance, the cooperating interrupted skirts act as an bending stop when they come in contact with the opposite plate.

Figure 2:
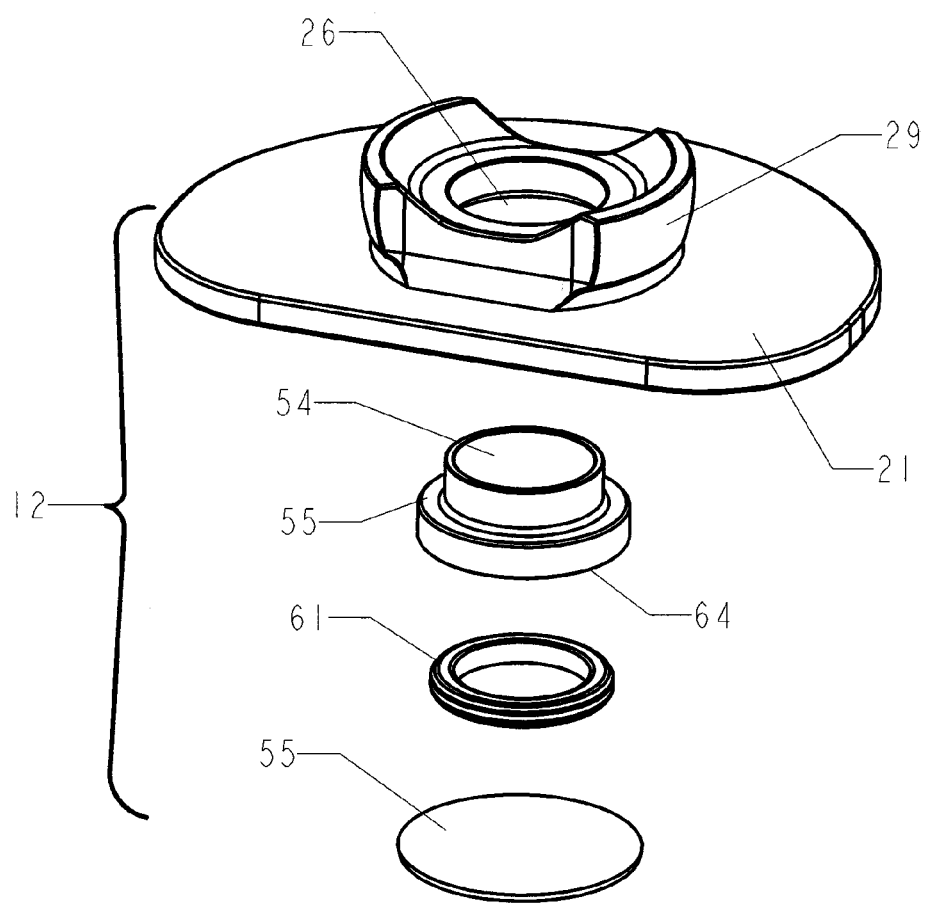
FIG. 2 is an exploded perspective of a disassembled plate of the spinal implant of FIG. 1.

FIG. 4 also illustrates a modification of the dynamic spring action of the implant of FIG. 2. The depression 52 is formed on a slidable sleeve 51 in a bore 13 of the plate. The sleeve 51 is solidly mounted in the bore 13. The sleeve 51 may be formed integrally with the dome cover plate as a one piece component, in which case, the plug is then laser welded or otherwise bonded into the plate 11. Plate 12 may be formed in the same fashion. This embodiment is less complex and less expensive to fabricate. It does not have the dynamic characteristics of the implant containing the O-ring.

Figure 7:
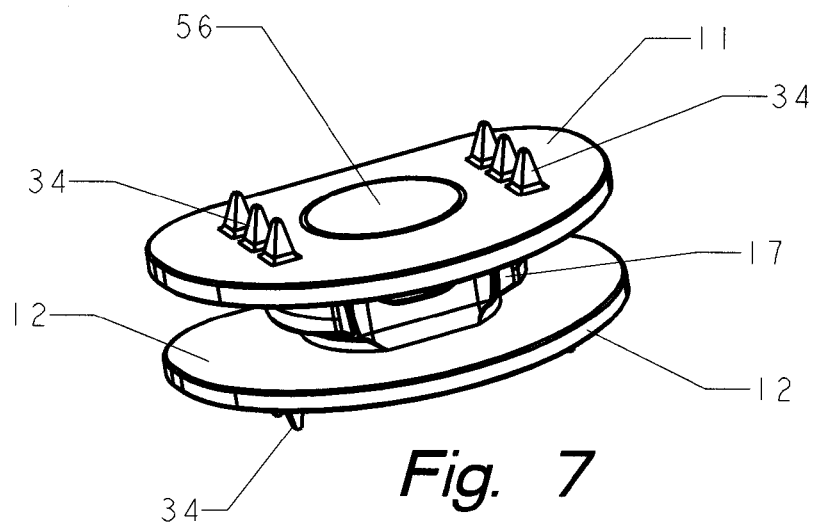
FIG. 7 is a perspective of the assembled implant of this invention showing a bone attachment device.
Figure 8:
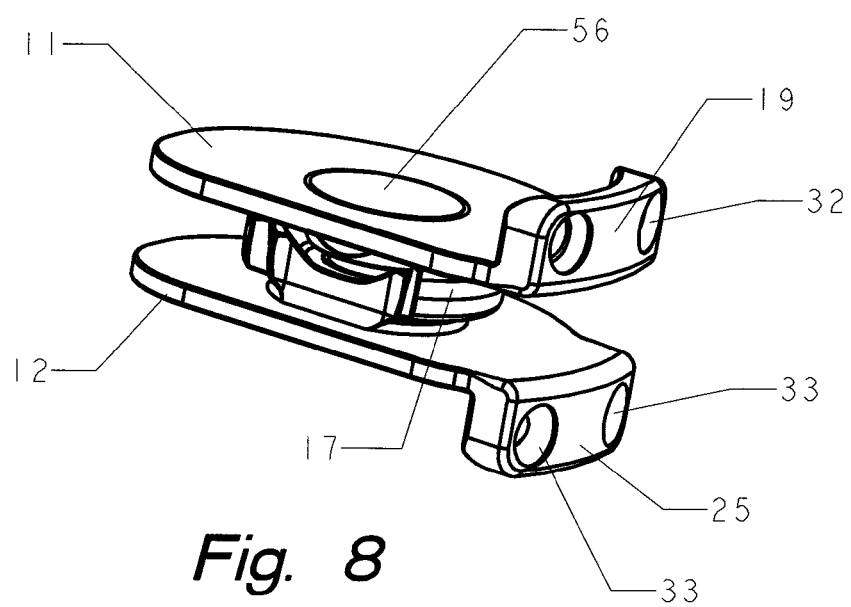
FIG. 8 is a perspective of the assembled implant of this invention showing another bone attachment device.

In FIG. 7, a fastener is shown in the form of spikes 34 attached or formed on flanges 19 and 25 which are to be driven into the end walls of the adjacent vertebra. As shown in FIG. 8, each of flanges 19 and 25 of the spinal implant has a vertical extension with apertures 32, 33 which cooperate with bone screws to mount the spinal implant on the vertebra. As shown, the vertical extensions are disposed in line with each other. However, the vertical extensions can be on opposite lateral sides of the flanges 19 and 25 permitting fastening of each plate on the opposite side of adjacent vertebrae. Of course, the two fasteners may be used together, eg., the spikes may be on one plate and the vertical extensions on the other plate of the same spinal implant.

The components are made from materials that are suitable for implantation in the living body and have the requisite strength to perform the described functions without deformation, e.g., the opposed bearing surfaces of the depressions and ball may be made of metal or a ceramic and a metal, respectively, the ceramic material is implant grade alumina ceramic or a silicon nitride or carbide and the metal may be a nitrogen alloyed chromium stainless steel or cobalt chrome alloy, or titanium, and alloys of each, coated metals, ceramics, ceramic coatings, and polymer coatings.

The plates may be made entirely of cobalt chrome alloy or only the inserts. In the high wear areas, such as the depressions coatings or inserts may be used to prevent galling and permit repair. In this modular concept, the end plates may be titanium, titanium alloy, or stainless steel among other materails as discussed above.

The prosthetic ball 50 is preferably made from an implant grade alumina ceramic or a silicon nitride or silicon carbide material. The ball 50 may be formed entirely of the ceramic material or a ceramic coating on another matrix. The alumina ceramic or silicon nitride or silicon carbide material can be hot isostatic pressed (HIPing). The ball 50 is then polished to a mirror-like finish. The ceramic ball is completely corrosion resistant and is non-abrasive. The solid matrix eliminates the wear particles, such as liberated from metal, other coated metals and polyethylene implants. The ball 50 has excellent thermal conductivity thereby reducing patient discomfort associated with exposure to cold weather. Further, the alumina ceramic or silicon nitride implant will react well with x-ray and MRI (magnetic resonance imaging) diagnostic procedures.

The kit contains plates with protrusions and skirts of varying lengths to allow selection of components for an implant with the axial dimension substantially the same as the thickness of the disk the implant will replace. The kit may also contain upper and lower plate components of varying sizes. A prosthesis could be assembled from the kit with springs in the upper and lower plates.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A spinal implant for placement between adjacent vertebrae to replace disk material comprising a first plate and a second plate adapted to interlock about a central axis, said first plate having a planar vertebrae engaging side and a disk side, a first interrupted skirt on said disk side extending approximately normal to said plate, said skirt formed as opposing separated arcs, a depression along said central axis of said disk side of said plate centrally located between said opposing arcs, said second plate having a second planar vertebrae engaging side and a second disk side, a second interrupted skirt on said second disk side extending approximately normal to said second plate, said second skirt formed as opposing separated arcs, a second depression along said central axis of said second disk side of said second plate centrally located between said opposing arcs and a universally rotatable ball captured in said depressions whereby said first plate is adapted to contact a vertebrae and said second plate is adapted to contact an adjacent vertebrae with said depressions each adapted to form a bearing surface for said ball along said central axis and said first and second interrupted skirts are interlocked forming a universal joint.

2. The spinal implant for placement between adjacent vertebrae of claim 1 wherein a spring located in said central axis is adapted to resiliently flex perpendicularly to said central axis whereby said first plate and said second plate are dynamically associated.

3. The spinal implant for placement between adjacent vertebrae of claim 2 wherein said first interrupted skirt and said second interrupted skirt are concentric in a plane parallel with said first and second plates, said opposed arcs of said first interrupted skirt are adapted to contact said opposed arcs of said second interrupted skirt.

4. The spinal implant for placement between adjacent vertebrae of claim 2 wherein said first plate includes a central bore, a sleeve secured in said bore, said depression formed in said sleeve, said spring secured in said bore.

5. The spinal implant for placement between adjacent vertebrae of claim 2 wherein said opposed arcs of said first interrupted skirt and said opposed arcs of said second interrupted skirt are concentric segments of a circle in a plane perpendicular to said first and second plates whereby said concentric segments of said first interrupted skirt are adapted to contact said concentric segments of said second interrupted skirt to form an interlocked universal joint.

6. The spinal implant for placement between adjacent vertebrae of claim 1 wherein said first interrupted skirt and said second interrupted skirt are concentric in a plane parallel with said first and second plates, said opposed arcs of said first interrupted skirt are adapted to contact said opposed arcs of said second interrupted skirt.

7. The spinal implant for placement between adjacent vertebrae of claim 1 wherein said opposed arcs of said first interrupted skirt and said second interrupted skirt extend approximately 90 degrees relative to each of said first interrupted skirt and said second interrupted skirt, respectively.

8. The spinal implant for placement between adjacent vertebrae of claim 1 wherein said first plate includes a central bore, a sleeve secured in said bore, said depression formed in said sleeve.

9. The spinal implant for placement between adjacent vertebrae of claim 1 wherein said opposed arcs of said first interrupted skirt and said opposed arcs of said second interrupted skirt are concentric segments of a circle in a plane perpendicular to said first and second plates whereby said concentric segments of said first interrupted skirt are adapted to contact said concentric segments of said second interrupted skirt to form an interlocked universal joint.

10. The spinal implant for placement between adjacent vertebrae of claim 1 wherein said first plate includes a cavity between said depression and said vertebrae side, an O-ring spring secured in said cavity, said ball adapted to flex said O-ring spring resulting in resilient compression.

11. The spinal implant for placement between adjacent vertebrae of claim 10 wherein said second plate includes a cavity between said second depression and said vertebrae side, an 0-ring spring secured in said cavity, said ball adapted to flex said 0-ring spring resulting in resilient compression.

12. The spinal implant f or placement between adjacent vertebrae of claim 1 wherein said second plate includes a cavity between said second depression and said vertebrae side, an O-ring spring secured in said cavity, said ball adapted to flex said 0-ring spring resulting in resilient compression.

13. The spinal implant for placement between adjacent vertebrae of claim 1 wherein a plurality of first plates of different sizes, a plurality of balls of different sizes and a plurality of second plates of different sizes comprise a kit whereby a proper sized spinal implant can be selected from said kit.

14. The spinal implant for placement between adjacent vertebrae of claim 1 wherein an elastic membrane extends between said first plate and said second plate about the periphery of said first plate and said second plate.

15. The spinal implant for placement between adjacent vertebrae of claim 14 wherein said elastic membrane is continuous and a viscous polymeric composition is located within said membrane.

16. A spinal implant for placement between adjacent vertebrae for resilient axial support comprising a first plate and a second plate, said first plate having a planar vertebrae engaging side and a disk side, a first fastener on said planar side for engaging a vertebrae, a first interrupted skirt on said disk side extending approximately normal to said plate, said first interrupted skirt formed as opposing arcs, a first centrally located bore in said first plate, a slidable sleeve in said bore, a depression in said disk side of said insert centrally located between said opposing arcs, said second plate having a second planar vertebrae engaging side and a second disk side, a second fastener on said second planar side for engaging a vertebrae, a second interrupted skirt on said second disk side extending approximately normal to said second plate, said second skirt formed as opposing arcs, a second centrally located bore in said second plate, a second sleeve in said second bore, a second depression on said second disk side of said second plate centrally located between said opposing arcs, a universally rotatable ball captured in said depression and said, second depression, said ball, said depression and said second depression each forming a bearing surface, a first cover plate mounted on said planar side of said first plate closing said bore and secured to said first plate, an O-ring spring for resilient compression between said insert and said cover plate, a second cover plate mounted on said planar side of said second plate closing said second bore and secured to said second plate, a second O-ring spring for resilient compression between said second insert and said second cover plate, said first interrupted skirt and said second interrupted skirt being concentric in a plane parallel with said first and second plates, said opposed arcs of said first interrupted skirt contacting said opposed arcs of said second interrupted skirt, said opposed arcs of said first interrupted skirt and said opposed arcs of said second interrupted skirt being concentric segments of a circle in a plane perpendicular to said first and second plates whereby said concentric segments of said first interrupted skirt contact said concentric segments of said second interrupted skirt to form an interlocked universal joint.

17. A method of assembling a resilient spinal implant comprising the steps of:
 a) providing a first plate, said first plate having a planar vertebrae engaging side and a disk side, a first interrupted skirt on said disk side extending approximately normal to said plate, said skirt formed as opposing separated arcs, a depression in said disk side of said plate centrally located between said opposing arcs,
 b) providing a second plate having a second planar vertebrae engaging side and a second disk side, a second interrupted skirt on said second disk side extending approximately normal to said second plate, said second skirt formed as opposing separated arcs, a second depression in said second disk side of said second plate centrally located between said opposing arcs,
 c) providing a ball and placing said ball in said depression,
 d) orienting said first plate and said second plate parallel with each other with said interrupted skirt of said first plate located between said opposing arcs of said second plate,
 e) moving said interrupted skirt of said first plate between said opposing arcs of said second plate to engage said ball into said depression and said second depression in axial alignment, and
 f) rotating said first plate with respect to said second plate about a central axis until said interrupted skirt of said first plate interlocks with said opposing arcs of said second plate.

18. A method of manufacture of a spinal prosthesis comprising the steps of:
 a) forming a plate having a planar surface and a periphery in the general shape of the end wall of a vertebra;
 b) forming a central through bore in said plate;
 c) forming a depending skirt on one side of said plate;
 d) forming an elongated sleeve having a depression in one end;
 e) inserting said sleeve in said through bore with said skirt being concentric with said depression;
 f) inserting a cover plate in said through bore and bonding said cover plate to said planar surface;
 g) forming a second plate having a second planar surface and a second periphery in the general shape of the end wall of a vertebra;
 h) forming a second central bore in said second plate;
 i) forming a second depending skirt on one side of said second plate between said second through bore and said second periphery, said second depending skirt having a lesser diameter than said depending skirt, said second depending skirt and said depending skirt being in contact with each other;
 j) forming a second elongated sleeve having a second depression in one end;
 k) inserting said second sleeve in said second through bore with said second skirt being concentric with said depression;
 l) inserting a second cover plate in said second through bore and bonding said second cover plate to said second planar surface; and
 m) forming a ball of a size closely approximating the size of said depression and said second depression.

19. The method of manufacture of a spinal prosthesis of claim 18 comprising the steps of:
 a) forming a cavity on the other end of said sleeve; and
 b) inserting an O-ring spring in said cavity whereby said sleeve is resiliently movable relative to said plate.

* * * * *